(12) United States Patent
Schelberger et al.

(10) Patent No.: US 6,444,692 B1
(45) Date of Patent: Sep. 3, 2002

(54) FUNGICIDAL MIXTURES

(75) Inventors: Klaus Schelberger, Gönnheim; Maria Scherer, Landau; Reinhold Saur, Böhl-Iggelheim; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,964

(22) PCT Filed: May 15, 1998

(86) PCT No.: PCT/EP98/02875

§ 371 (c)(1),
(2), (4) Date: Nov. 17, 1999

(87) PCT Pub. No.: WO98/53689

PCT Pub. Date: Dec. 3, 1998

(30) Foreign Application Priority Data

May 28, 1997 (DE) ......................................... 197 22 223

(51) Int. Cl.[7] ........................ A01N 43/64; A01N 43/56; A01N 43/06; A01N 37/34; A01N 37/18
(52) U.S. Cl. ........................ 514/384; 514/406; 514/407; 514/438; 514/539; 514/521; 514/617; 514/619
(58) Field of Search ................................ 514/407, 384, 514/539, 521, 619, 617, 406, 438

(56) References Cited

U.S. PATENT DOCUMENTS 6,156,796 A    12/2000   Sano et al. ................. 514/539

FOREIGN PATENT DOCUMENTS

| CA | 2194502 | 1/1996 |
|---|---|---|
| CA | 2194503 | 1/1996 |
| CA | 2208585 | 6/1996 |
| EP | 0253 213 | 1/1988 |
| EP | 0398 692 | 11/1990 |
| EP | 0477 631 | 4/1992 |
| EP | 0805148 | 11/1997 |
| WO | 96/01256 | 1/1996 |
| WO | 96/01258 | 1/1996 |
| WO | 97/46097 | 12/1997 |

*Primary Examiner*—Allen J. Robinson
(74) *Attorney, Agent, or Firm*—Keil & Weinkauf

(57) ABSTRACT

A fungicidal mixture, comprising at least one compound selected from a) carbamates of the formula I,

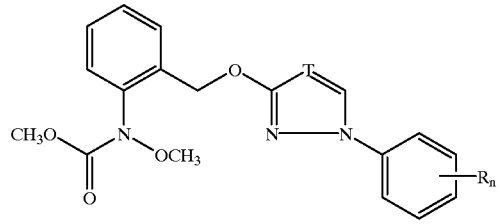

where T is CH or N, n is 0, 1 or 2 and R is halogen, $C_1$–$C_4$-alkyl or $C_1$–$C_4$-haloalkyl, it being possible for the radicals R to be different if n is 2, $a_2$) the oxime ether carboxylate of the formula II

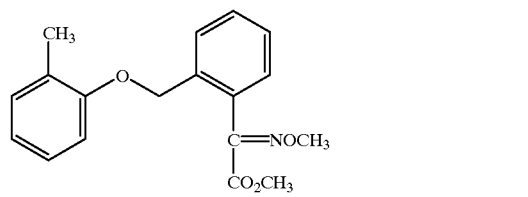

or $a_3$) the oxime ether carboxamide of the formula III,

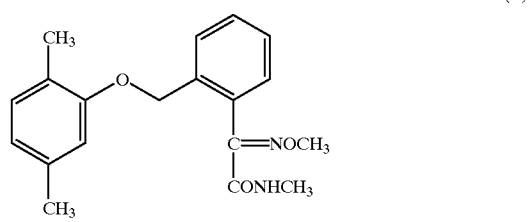

and b) a compound of the formula IV

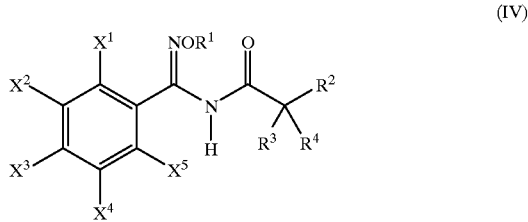

in a synergistically effective amount.

14 Claims, No Drawings

FUNGICIDAL MIXTURES

This application is a 371 of PCT/EP98/02875, filed May 15, 1998.

The present invention relates to a fungicidal mixture, comprising at least one compound selected from a₁) carbamates of the formula I,

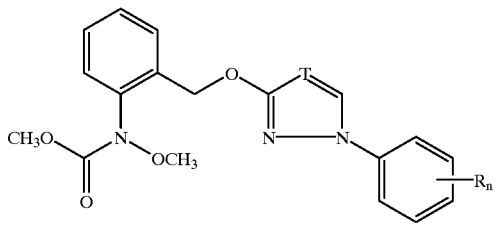

(I)

where T is CH or N, n is 0, 1 or 2 and R is halogen, $C_1$–$C_4$-alkyl or $C_1$–$C_4$-haloalkyl, it being possible for the radicals R to be different if n is 2, a₂) the oxime ether carboxylate of the formula II (II)

or a₃) the oxime ether carboxamide of the formula III, (III)

and b) at least one compound of the formula IV, (IV)

where the substituents $X^1$ to $X^5$ and $R^1$ to $R^4$ have the following meanings:

$X^1$ to $X^5$ independently of each other are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-thioalkoxy, $C_1$–$C_4$-sulfonylalkyl, nitro, amino, N-$C_1$–$C_4$-carboxylamino, N-$C_1$–$C_4$-alkylamino;

$R^1$ is $C_1$–$C_4$-alkyl, $C_2$–$C_4$-alkenyl, $C_2$–$C_4$-alkinyl, $C_1$–$C_4$-alkyl-$C_3$–$C_7$-cycloalkyl, it being possible for these radicals to carry substituents selected from the group consisting of halogen, cyano, and $C_1$–$C_4$-alkoxy, $R^2$ is a phenyl radical or a 5- or 6-membered saturated or unsaturated heterocyclyl radical having at least one hetero atom selected from the group consisting of N, O and S, it being possible for the cyclic radicals to have one to three substituents selected from the group consisting of halogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoxy-$C_2$–$C_4$-alkenyl, $C_1$–$C_4$-alkoxy-$C_2$–$C_4$-alkinyl, $R^3$ and $R^4$ independently of each other are each hydrogen, $C_1$–$C_4$-alkyl, $C_1$–$C_4$-alkoxy, $C_1$–$C_4$-alkylthio, N-$C_1$–$C_4$-alkylamino, $C_1$–$C_4$-haloalkyl or $C_1$–$C_4$-haloalkoxy in a synergistically effective amount.

Moreover, the invention relates to methods for controlling harmful fungi using mixtures of the compounds I, II and/or III and IV and to the use of the compounds I, II and/or III and IV for the preparation of such mixtures.

The compounds of the formula I, their preparation and their activity against harmful fungi are disclosed in the literature (WO-A 96/01,256 and 96/01,258).

The compounds of the formula II and III, their preparation and their activity against harmful fungi are disclosed in the literature (EP-A 253 213, EP-A 398 692 and EP-A 477631).

The compounds of the formula IV and processes for their preparation are described in WO-A 96/19442.

It was an object of the present invention to provide mixtures which have an improved activity against harmful fungi combined with a reduced total amount of active ingredients applied (synergistic mixtures), with a view to reducing the rates of application and to improving the spectrum of action of the known compounds.

Accordingly, we have found that this object is achieved by the mixtures defined at the outset. Moreover, we have found that better control of the harmful fungi is possible by applying the compounds I and II and/or III simultaneously together or separately, or by applying the compounds I and II and/or III in succession, than when the individual compounds are used.

The formula I represents in particular carbamates in which the combination of the substituents corresponds to one row of the table below:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |

TABLE 1-continued

| No. | T | $R_n$ |
|---|---|---|
| I.14 | N | 3-CH$_2$CH$_3$ |
| I.15 | N | 4-CH$_2$CH$_3$ |
| I.16 | N | 2-CH(CH$_3$)$_2$ |
| I.17 | N | 3-CH(CH$_3$)$_2$ |
| I.18 | N | 4-CH(CH$_3$)$_2$ |
| I.19 | N | 2-CF$_3$ |
| I.20 | N | 3-CF$_3$ |
| I.21 | N | 4-CF$_3$ |
| I.22 | N | 2,4-F$_2$ |
| I.23 | N | 2,4-Cl$_2$ |
| I.24 | N | 3,4-Cl$_2$ |
| I.25 | N | 2-Cl, 4-CH$_3$ |
| I.26 | N | 3-Cl, 4-CH$_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-CH$_3$ |
| I.37 | CH | 3-CH$_3$ |
| I.38 | CH | 4-CH$_3$ |
| I.39 | CH | 2-CH$_2$CH$_3$ |
| I.40 | CH | 3-CH$_2$CH$_3$ |
| I.41 | CH | 4-CH$_2$CH$_3$ |
| I.42 | CH | 2-CH(CH$_3$)$_2$ |
| I.43 | CH | 3-CH(CH$_3$)$_2$ |
| I.44 | CH | 4-CH(CH$_3$)$_2$ |
| I.45 | CH | 2-CF$_3$ |
| I.46 | CH | 3-CF$_3$ |
| I.47 | CH | 4-CF$_3$ |
| I.48 | CH | 2,4-F$_2$ |
| I.49 | CH | 2,4-Cl$_2$ |
| I.50 | CH | 3,4-Cl$_2$ |
| I.51 | CH | 2-Cl, 4-CH$_3$ |
| I.52 | CH | 3-Cl, 4-CH$_3$ |

Particular preference is given to the compounds I.12, I.23, I.32 and I.38.

In relation to the C=Y or C=CH or C=N double bonds, the compounds of the formulae I to III can be present in the E or the Z configuration (in relation to the carboxylic acid function). Accordingly, they can be used in the mixture according to the invention in each case either in the form of the pure E or Z isomers or in the form of an E/Z isomer mixture.

The E/Z isomer mixture or the Z isomer is preferably used, the Z isomer being especially preferred.

The C=N double bonds of the oxime ether groups in the side chain of the compounds I to III can exist in each case in the form of pure E or Z isomers or as E/Z isomer mixtures. The compounds I to III can be used in the mixtures according to the invention both as isomer mixtures and as pure isomers. With a view to their use, compounds I to III which are particularly preferred are those where the terminal oxime ether group in the side chain is in the cis configuration (OCH$_3$ to ZR').

Owing to their basic character, the compounds I to III are capable of forming salts or adducts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, for example p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth subgroup, in particular chromium, manganese, iron, cobalt, nickel, copper, zinc and others. Especially preferred are the metal ions of the elements of the subgroups of the fourth period. The metals can exist in the various valences which they can assume.

Among the compounds of the formula IV, those are preferred where $X^1$ is a $C_1$–$C_4$-haloalkyl group, in particular a trifluoromethyl group, and $X^2$ and $X^3$ are hydrogen or a halogen group, in particular hydrogen. $X^4$ and $X^5$ are preferably hydrogen, halogen (in particular Cl or F), $C_1$–$C_4$-alkoxy (in particular methoxy or ethoxy), $C_1$–$C_4$-alkylthio (in particular methylthio or ethylthio), $C_1$–$C_4$-haloalkyl (in particular trifluoromethyl) or $C_1$–$C_4$-haloalkoxy (in particular trifluoromethoxy).

Preferred substituents $R^1$ are $C_1$–$C_4$-alkyl (methyl, ethyl, n- and i-propyl and t-butyl), $C_1$–$C_4$-alkylene-$C_3$–$C_7$-cycloalkyl, $C_1$–$C_4$-alkenyl (in particular ethenyl, propenyl and butenyl, in particular those which may be substituted by halogen (preferably Cl)), propinyl, cyanomethyl and methoxymethyl. Among the $C_1$–$C_4$-alkylene-$C_3$–$C_7$-cycloalkyl substituents, preference is given in particular to methylene-substituted compounds, in particular methylenecyclopropyl, methylenecyclopentyl, methylenecyclohexyl and methylenecyclohexenyl. The rings of these substituents may be substituted, preferably by halogen.

Suitable substituents $R^2$ are, in addition to phenyl (unsubstituted or substituted), in particular thienyl, pyrazolyl, pyrrolyl, imidazolyl, thiazolyl, furyl, pyridazinyl and pyrimidinyl. Preferred substituents on these ring systems are halogen (in particular F and Cl), $C_1$–$C_4$-alkoxy (in particular methoxy) and $C_1$–$C_4$-alkyl (in particular methyl, ethyl). The number of the ring substituents may be 1 to 3, in particular 1 to 2. Particular preference is given to phenyl or substituted phenyl.

Preferred substituents $R^3$ and $R^4$ are hydrogen, F, Cl, methyl, ethyl, methoxy, thiomethyl and N-methylamino. $R^3$ and $R^4$ together may additionally form a grouping=O.

Preferred compounds of formula IV are shown in the tables of the abovementioned WO 96/019442. Among these, the compounds listed in Table II below are particularly preferred ($R^3$ and $R^4$ are each hydrogen).

TABLE II

| No. | $X^1$ | $X^2$ | $X^3$ | $X^4$ | $X^5$ | $R^1$ | $R^2$ |
|---|---|---|---|---|---|---|---|
| II.1 | $CF_3$ | H | H | H | H | ethyl | Ph-4-OMe |
| II.2 | $CF_3$ | H | H | H | H | methyl | Ph-4-OMe |
| II.3 | $CF_3$ | H | H | H | H | —$CH_2$-cPr | 2-thienyl |
| II.4 | $CF_3$ | H | H | H | H | —$CH_2$-cPr | 3-thienyl |
| II.5 | $CF_3$ | H | H | H | H | —$CH_2$-cPr | Ph-2,4-$F_2$ |
| II.6 | $CF_3$ | H | H | H | H | —$CH_2$-cPr | Ph-2-F |
| II.7 | $CF_3$ | H | H | H | H | —$CH_2$-cPr | Ph-2-F-4-OMe |
| II.8 | $CF_3$ | H | H | H | H | —$CH_2$-cPr | Ph-3-Me |
| II.9 | $CF_3$ | H | H | H | H | —$CH_2$-cPr | Ph-3-Me-4-OMe |
| II.10 | $CF_3$ | H | H | H | H | —$CH_2$-cPr | Ph-4-F |
| II.11 | $CF_3$ | H | H | H | H | —$CH_2$-cPr | Ph-4-Me |
| II.12 | $CF_3$ | H | H | H | H | —$CH_2$-cPr | Ph-4-OMe |
| II.13 | $CF_3$ | H | H | H | H | —$CH_2$-cPr | Ph |
| II.14 | $CF_3$ | H | H | H | H | —$CH_2$—CH=$CH_2$ | Ph |
| II.15 | $CF_3$ | H | H | H | H | —$CH_2$—CH=$CH_2$ | Ph-4-OMe |
| II.16 | $CF_3$ | H | H | H | H | —$CH_2$—CH=$CCl_2$ | Ph-4-OMe |
| II.17 | $CF_3$ | H | H | H | H | —$CH_2$—$CH_3$ | Ph-4-OMe |
| II.18 | $CF_3$ | H | H | H | F | —$CH_2CH_3$ | Ph |
| II.19 | $CF_3$ | H | H | H | F | —$CH_3$ | Ph-4-OMe |
| II.20 | $CF_3$ | H | H | H | F | —$CH_2$-cPr | Ph |
| II.21 | $CF_3$ | H | H | H | F | —$CH_2$-cPr | Ph-2-F |
| II.22 | $CF_3$ | H | H | H | F | —$CH_2$-cPr | Ph-2,4-$F_2$ |
| II.23 | $CF_3$ | H | H | H | F | —$CH_2$-cPr | Ph-2-F-3-Me |
| II.24 | $CF_3$ | H | H | H | F | —$CH_2$-cPr | Ph-2-F-4-OMe |
| II.25 | $CF_3$ | H | H | H | F | —$CH_2$-cPr | Ph-3,5-$Me_2$ |
| II.26 | $CF_3$ | H | H | H | F | —$CH_2$-cPr | 3-methylpyrazol-1-yl |
| II.27 | $CF_3$ | H | H | H | F | —$CH_2$-cPr | 3-methyl-2-thienyl |
| II.28 | $CF_3$ | H | H | H | F | —$CH_2$-cPr | 2-thienyl |
| II.29 | $CF_3$ | H | H | H | F | —$CH_2$-cPr | 3-thienyl |
| II.30 | $CF_3$ | H | H | H | F | —$CH_2$—$CHF_2$ | Ph-4-OMe |
| II.31 | $CF_3$ | H | H | H | F | —$CH_2$—$OCH_3$ | Ph-4-OMe |
| II.32 | $CF_3$ | H | H | H | F | —$CH_2$—$OCH_3$ | Ph |
| II.33 | $CF_3$ | H | H | H | F | —$CH_2CN$ | Ph-4-Ome |
| II.34 | $CF_3$ | H | H | H | F | —$CH_2CN$ | Ph |
| II.35 | $CF_3$ | H | H | H | F | —$CH_2$—C≡CH | Ph |
| II.36 | $CF_3$ | H | H | H | F | —$CH_2$—C≡CH | Ph-4-OMe |
| II.37 | $CF_3$ | H | H | H | F | —$CH_2$—C≡CH | Ph-2-F |
| II.38 | $CF_3$ | H | H | H | F | —$CH_2$—C≡CH | Ph-4-Me |
| II.39 | $CF_3$ | H | H | H | F | —$CH_2$—C≡CH | 2-thienyl |
| II.40 | $CF_3$ | H | H | H | F | —$CH_2$—C≡CH | Ph-2-F-4-OMe |
| II.41 | $CF_3$ | H | H | H | F | i-propyl | Ph |
| II.42 | $CF_3$ | H | H | H | F | n-butyl | Ph |
| II.43 | $CF_3$ | H | H | H | F | n-propyl | Ph |
| II.44 | $CF_3$ | H | H | H | F | t-butyl | Ph |
| II.45 | $CF_3$ | H | H | H | Cl | —$CH_3$ |  |
| II.46 | $CF_3$ | H | H | H | Cl | —$CH_2CN$ | Ph-4-OMe |
| II.47 | $CF_3$ | H | H | H | Cl | —$CH_2$—OMe | Ph-4-OMe |
| II.48 | $CF_3$ | H | H | H | Cl | —$CH_2$-cPr | Ph |
| II.49 | $CF_3$ | H | H | H | Cl | —$CH_2$-cPr | 3-methylpyrazol-1-yl |
| II.50 | $CF_3$ | H | H | H | Cl | —$CH_2$-cPr | 2-thienyl |
| II.51 | $CF_3$ | H | H | H | Cl | —$CH_2$-cPr | Ph-2,4-$F_2$ |
| II.52 | $CF_3$ | H | H | H | Cl | —$CH_2$—C≡CH | Ph-4-OMe |
| II.53 | $CF_3$ | H | H | H | $CF_3$ | —$CH_3$ | Ph-4-OMe |
| II.54 | $CF_3$ | H | H | H | $CF_3$ | —$CH_2CH_2Cl$ | Ph-4-OMe |
| II.55 | $CF_3$ | H | H | H | $CF_3$ | —$CH_2$-cPr | 2-thienyl |
| II.56 | $CF_3$ | H | H | H | $CF_3$ | —$CH_2$-cPr | Ph-2-F-5-Me |
| II.57 | $CF_3$ | H | H | H | $CF_3$ | —$CH_2$-cPr | Ph-4-OMe |
| II.58 | $CF_3$ | H | H | H | $CF_3$ | —$CH_2$-cPr | Ph |
| II.59 | $CF_3$ | H | H | H | $OCH_3$ | —$CH_2CH_3$ | Ph-4-OMe |
| II.60 | $CF_3$ | H | H | H | $OCH_3$ | —$CH_2$-cPr | Ph-4-OMe |
| II.61 | $CF_3$ | H | H | H | $OCH_3$ | —$CH_2$-cPr | Ph |
| II.62 | $CF_3$ | H | H | H | $SCH_3$ | —$CH_2$-cPr | Ph |
| II.63 | $CF_3$ | H | H | H | $SCH_3$ | —$CH_2$-cPr | Ph-4-OMe |
| II.64 | $CF_3$ | H | H | Cl | F | —$CH_2$—$CH_2Cl$ | Ph |
| II.65 | $CF_3$ | H | H | Cl | F | —$CH_2$—CH=$CH_2$ | Ph-4-OMe |
| II.66 | $CF_3$ | H | H | Cl | F | —$CH_2$-cPr | 2-thienyl |
| II.67 | $CF_3$ | H | H | Cl | F | —$CH_2$-cPr | Ph-2-F |
| II.68 | $CF_3$ | H | H | Cl | F | —$CH_2$-cPr | Ph |
| II.69 | $CF_3$ | H | H | Cl | F | —$CH_2$-cPr | Ph-2-F-5-Me |
| II.70 | $CF_3$ | H | H | Cl | Cl | —$CH_2$—CH=$CH_2$ | Ph-4-OMe |
| II.71 | $CF_3$ | H | H | Cl | Cl | —$CH_2CH_2Cl$ | Ph |
| II.72 | $CF_3$ | H | H | Cl | Cl | —$CH_2CH_3$ | Ph-2-F-5-Me |
| II.73 | $CF_3$ | H | H | Cl | Cl | —$CH_2$-cPr | Ph-3,5-$Me_2$ |
| II.74 | $CF_3$ | H | H | $SCH_3$ | F | —$CH_2$-cPr | Ph-4-OMe |

TABLE II-continued

| No. | $X^1$ | $X^2$ | $X^3$ | $X^4$ | $X^5$ | $R^1$ | $R^2$ |
|---|---|---|---|---|---|---|---|
| II.75 | $CF_3$ | H | H | $OCH_3$ | F | —$CH_2$-cPr | Ph-4-OMe |
| II.76 | $CF_3$ | H | F | H | H | —$CH_2$-cPr | Ph |
| II.77 | $CF_3$ | H | F | H | H | —$CH_2$—$CH_3$ | Ph-4-OMe |
| II.78 | $CF_3$ | H | H | F | F | —$CH_2CH_3$ | Ph |
| II.79 | $CF_3$ | H | H | F | F | —$CH_2$—$CH_2Cl$ | Ph-2-F-5-Me |
| II.80 | $CF_3$ | H | H | F | F | —$CH_2$—$OCH_3$ | Ph-4-OMe |
| II.81 | $CF_3$ | H | H | F | F | —$CH_2$-cPr | Ph |
| II.82 | $CF_3$ | H | H | F | F | —$CH_2$-cPr | 3-methylpyrazol-1-yl |
| II.83 | $CF_3$ | H | H | F | F | —$CH_2$-cPr | 3-methyl-2-thienyl |
| II.84 | $CF_3$ | H | H | F | F | —$CH_2$-cPr | Ph-2-F-3-Me |
| II.85 | $CF_3$ | H | H | F | F | —$CH_2$-cPr | Ph-2-F-4-OMe |
| II.86 | $CF_3$ | H | H | F | F | —$CH_2$-cPr | Ph-2-F-5-Me |
| II.87 | $CF_3$ | H | H | F | F | —$CH_2$-cPr | Ph-4-OMe |
| II.88 | $CF_3$ | H | H | F | F | —$CH_2$-cPr | Ph-4F |
| II.89 | $CF_3$ | H | H | F | F | i-propyl | Ph-4-OMe |
| II.90 | $CF_3$ | H | H | F | F | n-Butyl | Ph-4-OMe |
| II.91 | $CF_3$ | H | H | F | F | —$CH_2$—C≡CH | Ph-4-OMe |
| II.92 | $CF_3$ | H | H | $CF_3$ | F | —$CH_3$ | Ph-4-OMe |
| II.93 | $CF_3$ | H | H | $CF_3$ | F | —$CH_2$—CH=$CH_2$ | Ph |
| II.94 | $CF_3$ | H | H | $CF_3$ | F | —$CH_2$-cPr | Ph |
| II.95 | $CF_3$ | H | H | Cl | Cl | —$CH_2$—CHxe-3 | Ph |
| II.96 | $CF_3$ | H | H | F | H | —$CH_2$-cPr | Ph-4-F |
| II.97 | $CF_3$ | H | H | Cl | Cl | —$CH_2$-cHex | Ph |
| II.98 | $CF_3$ | H | H | H | F | —$CH_2$—$SCH_3$ | Ph |
| II.99 | $CF_3$ | H | H | H | F | —$CH_2$—$SOCH_3$ | Ph |
| II.100 | $CF_3$ | H | H | H | F | —$CH_2$—$SO_2CH_3$ | Ph |
| II.101 | $CF_3$ | H | H | H | F | —$CH_2$—NHMe | Ph |
| II.102 | $CF_3$ | H | H | H | F | $CH_2$—$CONH_2$ | Ph |
| II.103 | $CF_3$ | H | H | H | F | $CH_2CON(CH_3)_2$ | Ph |

In the table above, cPr is cyclopropyl, cHxe-n is cyclohexenyl unsaturated in position n, c-Hex is cyclohexyl and Ph is phenyl.

Particular preference is given to compounds IV in which $R^1$ is a radical $CH_2$-cPr and $R^2$ is an unsubstituted or substituted phenyl radical. Among these, preference is given to compounds in which $X^4$ and $X^5$ are each halogen, preferably F. The physical data of these compounds and processes for their preparation are given in the abovementioned WO 94/19442.

When preparing the mixtures, it is preferred to employ the pure active ingredients I, II and/or III and IV, to which further ingredients active against harmful fungi or other pests, such as insects, arachnids or nematodes, or else herbicidal or growth-regulating active ingredients or fertilizers can be admixed, if so required.

The mixtures of the compounds I, II and/or III and IV, or the simultaneous joint or separate use of the compounds I, II and/or III and IV, have outstanding action against a wide spectrum of phytopathogenic fungi, in particular from the classes of the Ascomycetes, Deuteromycetes, Phycomycetes and Basidiomycetes. Some of them act systemically and can therefore be employed as folia- and soil-acting fungicides.

They are especially important for controlling the large number of fungi in a variety of crop plants, such as cotton, vegetable species (e.g. cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and Sphaerotheca fuliginea in cucurbits, *Podosphaera leucotricha* in apples, Uncinula necator in grapevines, Puccinia species in cereals, Rhizoctonia species in cotton, rice and lawn, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, Pseudoperonospora species in cucurbits and hops, *Plasmopara viticola* in grapevines, Alternaria species in vegetables and fruit and Fusarium and Verticillium species.

Furthermore, they can be used in the protection of materials (e.g. in the protection of wood), for example against *Paecilomyces variotii*.

The compounds I, II and/or III and IV can be applied simultaneously together or separately or in succession, the sequence, in the case of separate application, generally not having any effect on the result of the control measures.

The compounds I, II and/or III and IV are usually used in a weight ratio of from 0.01:1 to 1:1, preferably from 0.03:1 to 0.5:1, in particular from 0.05:1 to 0.5:1 (IV:I, II and/or III).

The application rates of the mixtures according to the invention are, in the case of the compounds I, II and/or III, from 0.005 to 0.5 kg/ha, preferably from 0.05 to 0.5 kg/ha, in particular from 0.05 to 0.2 kg/ha, depending on the nature of the desired effect.

Correspondingly, in the case of the compounds IV, the application rates are generally from 0.001 to 0.2 kg/ha, preferably from 0.001 to 0.1 kg/ha, in particular from 0.005 to 0.05 kg/ha.

For seed treatment, the application rates of the mixture are generally from 0.001 to 100 g/kg of seed, preferably from 0.01 to 50 g/kg, in particular from 0.01 to 10 g/kg.

If phytopathogenic harmful fungi are to be controlled, the separate or joint application of the compounds I and II or of the mixtures of the compounds I, II and/or III and IV is effected by spraying or dusting the seeds, the plants or the soils before or after sowing of the plants, or before or after plant emergence.

The fungicidal synergistic mixtures according to the invention, or the compounds I, II and/or III and IV, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a manner known per se, e.g. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-,hepta- and octadecanols or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I and II or III or IV or the mixture of the compounds I and II, III or IV with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I, II, III and/or IV or of the mixture of the compounds I, II and/or III and IV. The active ingredients are employed in a purity of from 90% to 100%, preferably from 95% to 100% (according to NMR spectrum or HPLC).

The compounds I, II and/or III or IV, or the mixtures, or the corresponding formulations, are applied by treating the harmful fungi or the plants, seeds, soils, areas, materials or spaces to be kept free from them with a fungicidally effective amount of the mixture, or the compounds I, II and/or III and IV in the case of separate applications. Application can be effected before or after infection by the harmful fungi.

The fungicidal activity of the compound and the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

USE EXAMPLE 1

Activity Against Powdery Mildew of Wheat

Leaves of wheat seedlings cv. "Frühgold" which had been grown in pots were sprayed to runoff point with an aqueous preparation of active ingredient which had been prepared from a stock solution comprising 10% of active ingredient, 63% of cyclohexanone and 27% of emulsifier and, 24 hours after the spray coating had dried on, dusted with spores of powdery mildew of wheat (*Erysiphe graminis* forma specialis tritici). The test plants were subsequently placed in a greenhouse at from 20 to 240° C. and a relative atmospheric humidity of 60 to 90%. After 7 days, the extent of mildew development was determined visually as % infection of the total leaf area.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colbys formula:

$$E = x + y + z - x \cdot y \cdot z / 100$$

E expected efficacy, expressed in % of the untreated control, when using the mixture of the active ingredients A, B and C at the concentrations a, b and c x efficacy, expressed in % of the untreated control, when using active ingredient A at a concentration of a y efficacy, expressed in % of the untreated control, when using active ingredient B at a concentration of b z efficacy, expressed in % of the untreated control, when using active ingredient C at a concentration of c The efficacy (E) is calculated as follows using Abbot's formula:

$$E = (1-\alpha) \cdot 100 / \beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The test results are shown in Tables 2 and 3 below.

TABLE 2

| Ex. | Active ingredient | Concentration of active ingredient in the spray liquor in ppm | Efficacy in % of the untreated control |
|---|---|---|---|
| 1V | Control (untreated) | (100% infection) | 0 |
| 2V | Compound I.32 | 0.5 | 10 |
|    |               | 0.125 | 0 |
| 3V | Compound II | 0.125 | 0 |

TABLE 2-continued

| Ex. | Active ingredient | Concentration of active ingredient in the spray liquor in ppm | Efficacy in % of the untreated control |
|---|---|---|---|
| 4V | Compound III | 0.125 | 20 |
| 5V | Compound II.81 | 0.5 | 70 |
|  |  | 0.125 | 70 |

TABLE 3

| Mixtures according to the invention | Observed efficacy | Calculated efficacy *) |
|---|---|---|
| 0.5 ppm I.32 + 0.5 ppm II.81 (Mixture 1:1) | 97 | 73 |
| 0.125 ppm I.32 + 0.125 ppm II.81 (Mixture 1:1) | 93 | 70 |
| 0.125 ppm II + 0.125 ppm II.81 (Mixture 1:1) | 90 | 70 |
| 0.125 ppm III + 0.125 ppm II.81 (Mixture 1:1) | 97 | 76 |

*) calculated using Colby's formula

The test results show that for all mixing ratios the observed efficacy is higher than the efficacy which had been calculated beforehand using Colby's formula.

What is claimed is:

1. A fungicidal composition comprising synergistically effective amounts of a component A) and a component B), wherein a) component A is a$_1$) at least one compound selected from a group consisting of carbamates of formula I,

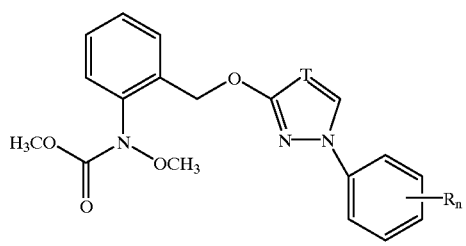

(I)

where T is CH or N, n is 0, 1 or 2 and R is halogen, $C_1$–$C_4$-alkyl or $C_1$–$C_4$-haloalkyl, and where the radicals R are identical or different if n is 2, and optionally one or both of the following compounds:

a$_2$) an oxime ether carboxylate of formula II

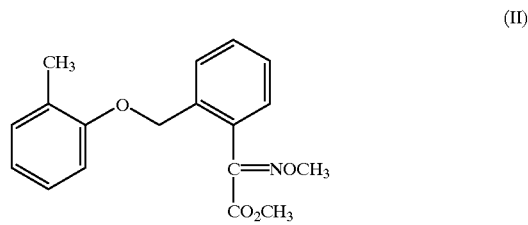

(II)

and a$_3$) an oxime ether carboxamide of formula III,

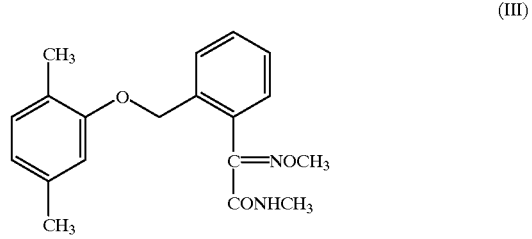

(III)

and b) component B is at least one compound of formula IV

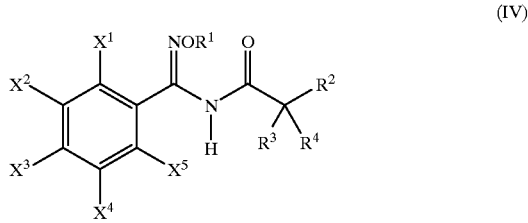

(IV)

wherein $X^1$ is $C_1$–$C_4$-haloalkyl or $C_1$–$C_4$-haloalkoxy;

$X^2$ and $X^3$ are each hydrogen;

$X^4$ and $X^5$ are independently of each other halogen;

$R^1$ is $C_1$–$C_4$-alkylene-$C_3$–$C_7$-cycloalkyl;

$R^2$ is a phenyl radical which is unsubstituted or substituted by one to three substituents selected from the group consisting of halogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoxy-$C_2$–$C_4$-alkenyl and $C_1$–$C_4$-alkoxy-$C_2$–$C_4$-alkinyl, $R^3$ is hydrogen, and $R^4$ is hydrogen, halogen, $C_1$–$C_4$-alkyl, $C_1$–$C_4$-alkoxy, $C_1$–$C_4$-alkylthio, N-$C_1$–$C_4$-alkylamino, $C_1$–$C_4$-haloalkyl or $C_1$–$C_4$-haloalkoxy.

2. The composition defined in claim 1, wherein component A comprises the oxime ether carboxylate of formula II or the oxime ether carboxamide of formula III.

3. The composition defined in claim 1, wherein component A comprises the oxime ether carboxylate of formula II and the oxime ether carboxamide of formula III.

4. A method for controlling harmful fungi, which comprises treating the harmful fungi, their habitat or plants, seeds, soils, areas, materials or spaces to be kept free from said fungi with synergistically effective amounts of component A and component B, wherein the components A and B are as set forth in claim 1.

5. The method of claim 4, wherein the component A is applied in an amount of from 0.005 to 0.5 kg/ha.

6. The method of claim 5, wherein the component B is applied in an amount of from 0.001 to 0.2 kg/ha.

7. The method of claim 4, wherein the component A is applied in an amount of from 0.005 to 0.5 kg/ha.

8. The method of claim 4, wherein the component B is applied in an amount of from 0.001 to 0.2 kg/ha.

9. The method claim 4, wherein component A comprises the oxime ether carboxylate of formula II or the oxime ether carboxamide of formula III.

10. The method of claim 9, wherein the component A is applied in an amount of from 0.005 to 0.5 kg/ha.

11. The method of claim 9, wherein the component B is applied in an amount of from 0.001 to 0.2 kg/ha.

12. The method claim 4, wherein component A comprises the oxime ether carboxylate of formula II and the oxime ether carboxamide of formula III.

13. The method of claim 12, wherein the component A is applied in an amount of from 0.005 to 0.5 kg/ha.

14. The method of claim 12, wherein the component B is applied in an amount of from 0.001 to 0.2 kg/ha.

* * * * *